(12) United States Patent
Iwasa

(10) Patent No.: US 11,492,554 B2
(45) Date of Patent: Nov. 8, 2022

(54) METHOD FOR PRODUCING RECYCLED MATERIAL, AND TIRE AND METHOD FOR PRODUCING TIRE

(71) Applicant: SEKISUI CHEMICAL CO., LTD., Osaka (JP)

(72) Inventor: Koichiro Iwasa, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 17/121,506

(22) Filed: Dec. 14, 2020

(65) Prior Publication Data

US 2021/0095210 A1 Apr. 1, 2021

Related U.S. Application Data

(63) Continuation of application No. 14/652,443, filed as application No. PCT/JP2013/083050 on Dec. 10, 2013, now Pat. No. 10,899,968.

(51) Int. Cl.
| | |
|---|---|
| C10B 53/07 | (2006.01) |
| C07C 29/15 | (2006.01) |
| C07C 1/20 | (2006.01) |
| C07C 29/151 | (2006.01) |
| C08F 236/10 | (2006.01) |
| C12P 5/00 | (2006.01) |
| B29D 30/00 | (2006.01) |
| C08J 11/12 | (2006.01) |
| C07C 39/12 | (2006.01) |
| C07C 47/21 | (2006.01) |
| C07C 55/10 | (2006.01) |

(52) U.S. Cl.
CPC .............. *C10B 53/07* (2013.01); *B29D 30/00* (2013.01); *C07C 1/20* (2013.01); *C07C 29/1518* (2013.01); *C07C 39/12* (2013.01); *C07C 47/21* (2013.01); *C07C 55/10* (2013.01); *C08F 236/10* (2013.01); *C08J 11/12* (2013.01); *C12P 5/007* (2013.01); *C08J 2319/00* (2013.01); *C08J 2321/00* (2013.01); *Y02P 20/143* (2015.11); *Y02W 30/62* (2015.05)

(58) Field of Classification Search
CPC ... C01B 3/36; C01B 53/07; C07C 1/20; C08F 236/10
See application file for complete search history.

(56) References Cited

U.S. PATENT DOCUMENTS

| | | | | |
|---|---|---|---|---|
| 5,294,663 | A * | 3/1994 | Fabris | C08L 9/00 524/526 |
| 8,863,518 | B2 | 10/2014 | Koseoglu | |
| 2005/0000162 | A1 | 1/2005 | Bishop et al. | |
| 2006/0169390 | A1 | 8/2006 | Galimberti et al. | |
| 2007/0032593 | A1 | 2/2007 | Yagi et al. | |
| 2010/0012256 | A1 | 1/2010 | Nakajima | |
| 2010/0216958 | A1 * | 8/2010 | Peters | C07C 17/02 526/258 |
| 2010/0249353 | A1 | 9/2010 | MacIntosh et al. | |
| 2011/0200518 | A1 | 8/2011 | MacIntosh et al. | |
| 2012/0073292 | A1 | 3/2012 | Koseoglu | |
| 2013/0090445 | A1 | 4/2013 | Hattori et al. | |
| 2014/0234926 | A1 * | 8/2014 | Beck | C12N 15/52 435/146 |

FOREIGN PATENT DOCUMENTS

| | | |
|---|---|---|
| CN | 1729095 A | 2/2006 |
| CN | 1908047 A | 2/2007 |
| JP | 2008-169330 A | 7/2008 |
| JP | 2010-275490 A | 12/2010 |
| JP | 2011-219522 A | 11/2011 |
| JP | 2012-153654 A | 8/2012 |
| JP | 2012-518658 A | 8/2012 |
| JP | 2012-521443 A | 9/2012 |
| WO | WO-2008/065951 A1 | 6/2008 |
| WO | WO-2009/154788 A2 | 12/2009 |
| WO | WO-2011/129878 A2 | 10/2011 |
| WO | WO-2011/129878 A3 | 10/2011 |
| WO | WO-2011129878 A2 * | 10/2011 ............... C12P 7/08 |
| WO | WO-2012/015340 A1 | 2/2012 |

OTHER PUBLICATIONS

Worden, R. M. et al., "Production of butanol and ethanol from synthesis gas via fermentation", Fuel, IPC Science and Technology Press, 1991, vol. 70, No. 5, pp. 615-619.

Lee, Jong Min et al., "Pyrolysis of waste tires with partial oxidation in a fluidized-bed reactor", Energy, 1995, vol. 20, No. 10, pp. 969-976.

Lindberg, Pia et al., "Engineering a platform for photosynthetic isoprene production in cyanobacteria, using *Synechocystis* as the model organism", Metabolic Engineering, 2010, vol. 12, pp. 70-79.

International Search Report for the Application No. PCT/JP2013/083050 dated Mar. 25, 2014.

International Preliminary Report on Patentability (PCT/IPEA/409) for Application No. PCT/JP2013/083050 dated Jan. 7, 2015 (English Translation mailed Jul. 23, 2015).

The First Office Action for the Application No. 201380054876.8 from The State Intellectual Property Office of the People's Republic of China dated May 3, 2016.

(Continued)

*Primary Examiner* — Youngsul Jeong
(74) *Attorney, Agent, or Firm* — Cheng Law Group, PLLC

(57) ABSTRACT

There is provided a method for producing a recycled material, whereby a recycled material can be efficiently obtained from a tire. The method for producing a recycled material according to the present invention includes a step of subjecting a tire to a gasification treatment to generate a gas containing a C1 gas from the tire, and a step of obtaining a recycled material containing at least one species selected from the group consisting of isoprene, butadiene, a butanediol compound, a butanol compound, a butenal compound, succinic acid, and polymers of these compounds by using the gas containing the C1 gas.

4 Claims, No Drawings

(56) References Cited

OTHER PUBLICATIONS

Supplementary European Search Report for the Application No. EP 13 872 752.4 dated Aug. 30, 2016.
European Office Action for Application No. EP 13 872 752.4 dated Sep. 21, 2017.
European Office Action for Application No. EP 13 872 752.4 dated Feb. 28, 2019.
Examination Report for Application No. 1738/KOLNP/2015 from the Intellectual Property India Office dated Jun. 17, 2019.

* cited by examiner

METHOD FOR PRODUCING RECYCLED MATERIAL, AND TIRE AND METHOD FOR PRODUCING TIRE

CROSS-REFERENCE TO RELATED APPLICATIONS

This application is a Continuation Application of patent application Ser. No. 14/652,443, filed on Jun. 15, 2015, which is a 371 application of Application Serial No. PCT/JP2013/083050, filed on Dec. 10, 2013, which is based on Japanese Patent Application No. 2013-010393, filed on Jan. 23, 2013, the entire contents of which are hereby incorporated by reference.

TECHNICAL FIELD

The present invention relates to a method for producing a recycled material by which method a recycled material is obtained from a tire. The present invention also relates to a tire and a method for producing a tire using the recycled material. Moreover, the present invention relates to a novel method for producing a tire.

BACKGROUND ART

For vehicles such as automobiles, tires made of rubber and having grooves on their surfaces are used with air filled therein. When tires on a vehicle have been used for a long period of time, grooves on their surfaces are shallowed and it becomes necessary to exchange the tires. As a result of the exchange, used waste tires are generated.

Used waste tires are often discarded. Accordingly, there is a problem that a large burden is placed on the environment. When a waste tire is discarded, a disposal cost is needed or the waste tire must be discarded in distinction from common garbage in a specific manner. In other words, discard of waste tires requires a cost and a labor. In order to reduce the cost and the labor, waste tires are sometimes illegally dumped and such illegal dumping of waste tires has become a substantial concern.

On the other hand, considerations have been made to regeneration and use of waste tires. Heretofore, as a method for regenerating a waste tire, there has been used a method in which a grooved part of the surface of a tire is scraped off and then a new rubber member is bonded to a thus-exposed surface, thereby reforming grooves on a surface. Such a method has been disclosed, for example, in Patent Document 1 cited below.

RELATED ART DOCUMENT

Patent Document

Patent Document 1: WO 2008/065951 A1

SUMMARY OF THE INVENTION

Problems to be Solved by the Invention

Since a rubber component is bonded to a surface of a waste tire in conventional methods for regenerating a waste tire such as that disclosed in Patent Document 1, the adhesion of a rubber component can be problematic with the methods. Moreover, in the conventional methods for regenerating a waste tire, since degradation of rubber components of parts other than the surface of a tire also has advanced due to a long period of use of the tire, there is a limit on the number of time of regeneration and reuse. Moreover, in the case where the surface of a waste tire has already been much shaved, the waste tire may not be successfully regenerated and therefore a waste tire may not be efficiently regenerated.

Accordingly, conventional methods for regenerating a waste tire are problematic in that waste tires cannot be regenerated and reused sufficiently and efficiently.

A main object of the present invention is to provide a method for producing a recycled material, the method being capable of efficiently affording a recycled material from a tire, and provide a tire and a method for producing a tire using a resulting recycled material. Another main object of the present invention is to provide a novel method for producing a tire, the method being capable of efficiently affording a tire.

Moreover, a limited object of the present invention is to provide a method for producing a recycled material, a tire, and a method for producing a tire, these being capable of effectively using a waste tire as a resource and reducing an environmental burden.

Means for Solving the Problems

According to a wide aspect of the present invention, there is provided a method for producing a recycled material, the method comprising: a step of subjecting a tire to a gasification treatment to generate a gas comprising a C1 gas from the tire, and a step of obtaining a recycled material comprising at least one species selected from the group consisting of isoprene, butadiene, a butanediol compound, a butanol compound, a butenal compound, succinic acid, and polymers of these compounds by using the gas comprising the C1 gas.

In a specific aspect of the method for producing a recycled material according to the present invention, the tire to be used for the gasification treatment is a waste tire.

In a specific aspect of the method for producing a recycled material according to the present invention, the gas comprising the C1 gas comprises $CO_x$ gas ($1 \leq x \leq 2$) and hydrogen gas.

In a specific aspect of the method for producing a recycled material according to the present invention, the recycled material comprises at least one species selected from the group consisting of isoprene, butadiene, and polymers of these compounds.

According to a wide aspect of the present invention, there is provided a tire obtained by using a recycled material obtained by the above-described method for producing a recycled material.

According to a wide aspect of the present invention, there is provided a method for producing a tire, the method comprising a step of obtaining a tire by using a recycled material obtained by the above-described method for producing a recycled material.

According to a wide aspect of the present invention, there is provided a method for producing a tire, the method comprising a step of obtaining a tire material comprising at least one species selected from the group consisting of isoprene, butadiene, a butanediol compound, a butanol compound, a butenal compound, succinic acid, and polymers of these compounds by using a gas comprising a C1 gas, and a step of obtaining a tire by using the tire material.

In a specific aspect of the method for producing a tire according to the present invention, the method further comprises a step of subjecting a tire to a gasification treatment to generate the gas comprising the C1 gas from the tire, wherein the tire material is a recycled tire material.

In a specific aspect of the method for producing a tire according to the present invention, the tire to be used for the gasification treatment is a waste tire.

In a specific aspect of the method for producing a tire according to the present invention, the gas comprising the C1 gas comprises $CO_x$ gas ($1 \leq x \leq 2$) and hydrogen gas.

In a specific aspect of the method for producing a tire according to the present invention, the tire material comprises at least one species selected from the group consisting of isoprene, butadiene, and polymers of these compounds.

Effect of the Invention

Since the method for producing a recycled material according to the present invention comprises a step of subjecting a tire to a gasification treatment to generate a gas comprising a C1 gas from the tire, and a step of obtaining a recycled material comprising at least one species selected from the group consisting of isoprene, butadiene, a butanediol compound, a butanol compound, a butenal compound, succinic acid, and polymers of these compounds by using the gas comprising the C1 gas, a recycled material capable of being used for the production of a tire or the like can be efficiently obtained.

Since the method for producing a tire according to the present invention comprises a step of obtaining a tire material comprising at least one species selected from the group consisting of isoprene, butadiene, a butanediol compound, a butanol compound, a butenal compound, succinic acid, and polymers of these compounds by using a gas comprising a C1 gas, and a step of obtaining a tire by using the tire material, a tire can be efficiently obtained.

MODE(S) FOR CARRYING OUT THE INVENTION

Hereafter, the present invention is described in detail.

The method for producing a recycled material according to the present invention includes a step of subjecting a tire to a gasification treatment to generate a gas containing a C1 gas from the tire, and a step of obtaining a recycled material containing at least one species selected from the group consisting of isoprene, butadiene, a butanediol compound, a butanol compound, a butenal compound, succinic acid, and polymers of these compounds by using the gas containing the C1 gas.

In the method for producing a recycled material according to the present invention, a recycled material can be obtained easily and efficiently from a tire because a gas containing a C1 gas is obtained from a tire and then a recycled material containing the above-specified components by using the gas containing the C1 gas. Since a recycled material containing components being to constitute a tire is obtained from a tire prior to a gasification treatment, the resulting recycled material can be suitably used for the production of a tire or the like.

Preferably, the recycled material is a recycled tire material. The recycled tire material is used for obtaining a retreaded tire. Preferably, the method for producing the recycled material is a method for producing a recycled material (recycled tire material) to be used for obtaining a retreaded tire.

The recycled material may be used for obtaining an item other from tires. Examples of the item other than tires include industrial rubber products such as a rubber sheet and a rubber hose.

Moreover, the present invention also provides a tire obtained using a recycled material obtained by the above-described method for producing a recycled material. Furthermore, the present invention also provides a method for producing a tire, the method comprising a step of obtaining a tire using a recycled material obtained by the above-described method for producing a recycled material. For tires obtained in such a manner, tires are used as a feedstock and tires such as waste tires, which are heretofore often discarded, are effectively used as a resource. Regeneration and reuse of tires such as waste tires can greatly reduce an environmental burden. Preferably, tires to be obtained using a recycled material are retreaded tires. For the retreaded tires, tires are used as a feedstock.

The method for producing a tire according to the present invention comprises a step of obtaining a tire material comprising at least one species selected from the group consisting of isoprene, butadiene, a butanediol compound, a butanol compound, a butenal compound, succinic acid, and polymers of these compounds by using a gas comprising a C1 gas, and a step of obtaining a tire by using the tire material.

In the method for producing a tire according to the present invention, a tire can be easily and efficiently obtained because a tire material containing the above-mentioned specific components is obtained using a gas comprising a C1 gas and a tire is obtained using the tire material.

Preferably, the method for producing a tire according to the present invention further comprises a step of subjecting a tire to a gasification treatment to generate a gas containing a C1 gas from the tire. The tire material is preferably a recycled tire material. Specifically, the method for producing a tire according to the present invention preferably comprises a step of subjecting a tire to a gasification treatment to generate a gas containing a C1 gas from the tire, a step of obtaining a tire material containing at least one species selected from the group consisting of isoprene, butadiene, a butanediol compound, a butanol compound, a butenal compound, succinic acid, and polymers of these compounds by using the gas containing the C1 gas, and a step of obtaining a tire using the tire material. In this case, since a retreaded tire is obtained using tires such as waste tires as a feedstock, waste tires, which are heretofore often discarded, can be effectively used as a resource. Regeneration and reuse of tires such as waste tires can greatly reduce an environmental burden.

Preferably, the tire prior to a gasification treatment (the tire to be used for a gasification treatment) is a waste tire. Preferably, the waste tire is a used tire. In the present invention, a waste tire can be used as a feedstock for a retreaded tire. Use of a waste tire as a feedstock for a retreaded tire can have no cost of disposal of waste tires. Moreover, use of a waste tire as a feedstock for a retreaded tire can greatly reduce a cost of producing the retreaded tire. In the present invention, since waste tires, which are heretofore often discarded, can be effectively used as a resource, an environmental burden can be reduced. In the present invention, since a waste tire itself serves as a resource, illegal dumping of waste tires can be reduced.

The tire prior to a gasification treatment may be a tire other than waste tires. Examples of the tire other than waste tires include defective tires or the like yielded during the production of a tire.

Preferably, the gas containing the C1 gas contains $CO_x$ gas ($1 \leq x \leq 2$) and hydrogen gas. x in the $CO_x$ gas is $1 \leq x \leq 2$. Preferably, the gas containing the C1 gas contains a mixed gas containing $CO_x$ gas ($1 \leq x \leq 2$) and hydrogen gas as main ingredients. In 100% by mass of the gas containing the C1 gas, the content of the mixed gas containing $CO_x$ gas (1≤x≤2) and hydrogen gas is preferably 50% by mass or more, more preferably 60% by mass or more, even more preferably 70% by mass or more, and particularly preferably 80% by mass or more.

The C1 gas is a gas of a compound whose number of carbon atom(s) is 1. Examples of the C1 gas include $CO_x$ gas (1≤x≤2) and methane. When obtaining a recycled material from the C1 gas, it may be used via an intermediate substance, such as formic acid and methanol. Examples of the compound to be transformed into the C1 gas include $CO_x$ (1≤x≤2) and methane. Preferably, the C1 gas is $CO_x$ gas. Examples of the $CO_x$ gas include carbon monoxide gas, carbon dioxide gas, and a mixed gas of carbon monoxide gas and carbon dioxide gas. When the $CO_x$ gas contains carbon monoxide gas and carbon dioxide gas in a molar ratio of 1:1, x is 1.5.

Specific examples of the gas containing the C1 gas include the gases provided below. It is noted that a gas other than the gases provided below may be used.

CO
$CO_2$
$CO/CO_2$
$CO/H_2$
$CO_2/H_2$
$CO/CO_2/H_2$

Examples of the above-mentioned method for generating a gas containing a C1 gas include a method of thermally decomposing a tire at high temperature. As to the method of thermally decomposing a tire at high temperature, specific examples of the above-mentioned method of generating a gas containing a C1 gas from a tire include a method of thermally decomposing a tire at a high temperature of about 1300° C. and also a method of thermally decomposing a tire at a temperature of about 800° C. using a catalyst.

The above-mentioned recycled material or the above-mentioned tire material contains at least one species selected from the group consisting of isoprene, butadiene, a butanediol compound, a butanol compound, a butenal compound, succinic acid, and polymers of these compounds. The polymer may be a homopolymer of any one selected from among isoprene, butadiene, a butanediol compound, a butanol compound, a butenal compound, and succinic acid and also may be a copolymer of at least two species selected from among isoprene, butadiene, a butanediol compound, a butanol compound, a butenal compound, and succinic acid. Examples of the butanediol compound include 1,4-butanediol, 2,3-butanediol, and 1,3-butanediol. Examples of the butanol compound include 1-butanol, 2-butanol, and isobutanol. Examples of the butenal compound include 2-butenal and 3-butenal. Accordingly, the recycled material or the tire material may contain at least one species selected from the group consisting of isoprene, butadiene, 1,4-butanediol, 2,3-butanediol, 1,3-butanediol, 1-butanol, 2-butanol, isobutanol, 2-butenal, 3-butenal, succinic acid, and polymers of these compounds.

When obtaining the recycled material or the tire material containing at least one species selected from among isoprene, butadiene, a butanediol compound, a butanol compound, a butenal compound, succinic acid, and polymers of these compounds using the above-mentioned gas containing a C1 gas, the production may be performed via an intermediate substance such as ethanol.

Since the recycled material or the tire material is suited for the production of a tire such as a retreated tire, it preferably contains at least one species selected from the group consisting of isoprene, butadiene, and polymers of these compounds. In this case, the polymer may be a homopolymer of isoprene or a homopolymer of butadiene and also may be a copolymer of isoprene and butadiene. In the polymer, a compound such as styrene may appropriately be copolymerized. Isoprene, butadiene, and (Co)polymers obtained from isoprene and butadiene are suited as base materials of tires. A copolymer obtained from isoprene or butadiene and styrene is also suited as a base material of a tire.

In the case where the recycled material or the tire material contains at least one species selected from the group consisting of isoprene, butadiene, and polymers of these compounds, the recycled material or the tire material may or may not contain at least one species selected from the group consisting of a butanediol compound, a butanol compound, a butenal compound, succinic acid, and polymers of these compounds. The recycled material or the tire material may contain at least one species selected from the group consisting of a butanediol compound, a butanol compound, a butenal compound, succinic acid, and polymers of these compounds.

The method for obtaining a recycled material or a tire material containing at least one species selected from the group consisting of isoprene, butadiene, a butanediol compound, a butanol compound, a butenal compound, succinic acid, and polymers of these compounds using the gas containing the C1 gas is not particularly restricted, and examples thereof include a chemical method using a metal catalyst and a biological method using a microbial catalyst. As to the metal catalyst, only one species may be used or alternatively two or more species may be used in combination. As to the microbial catalyst, only one species may be used or alternatively two or more species may be used in combination. Use of the metal catalyst and the microbial catalyst appropriately selected makes it possible to appropriately control the components contained in the recycled material or the tire material.

In the above-mentioned chemical method, specifically, ethanol can be synthesized from a $CO_x$ compound by, for example, use of an alloy containing rhodium metal as a catalyst and moreover butadiene can be synthesized by dimerizing the resulting ethanol by use of a metal catalyst at a high temperature.

In the above-mentioned biological method, specifically, isoprene can be synthesized from a $CO_x$ compound by, for example, use of a catalyst prepared by introducing a nucleic acid capable of coding isoprene synthase into a Clostridium microorganism that increases using a $CO_x$ compound as a feedstock.

In the step of obtaining a tire using the recycled tire material or the tire material, a tire can be obtained by reacting the recycled tire material or the tire material and molding it. Generally, in this reaction, the recycled tire material or the tire material undergoes a crosslinking reaction.

In the step of obtaining a tire, it is also permitted to use, in addition to the recycled tire material or the tire material, a tire constituent material other than the recycled tire material or the tire material.

Examples of the tire constituent material include a newly prepared tire feedstock, etc. It is also permitted to use a mixture of the recycled tire material or the tire material and a newly prepared tire feedstock. In this case, a higher use proportion of the recycled tire material or the tire material results in a reduced environmental burden and a reduced cost for a resulting retreaded tire. Examples of the tire feedstock include butadiene rubber, isoprene rubber, butadiene/styrene copolymer rubber, isoprene/styrene copolymer rubber, and butadiene/isoprene copolymer rubber.

Other examples of the tire constituent material include pigment, sulfur, and polyester compounds. The above-mentioned pigment is preferably a carbonaceous pigment and more preferably a carbon pigment. Specific examples of the pigment include carbon black, acetylene black, and Ketchen black.

Hereafter, the present invention is concretely described by way of examples. The present invention is not limited to the following examples.

Example 1

There was prepared a waste tire that had been used on a vehicle and had shallowed grooves on the surface thereof.

The waste tire was separated into a gas containing a C1 gas, carbonization carbon, and metallic components by heating it up to 1300° C. The generated gas containing the C1 gas contained 69% in molar ratio of $CO_x$ gas and 30% in molar ratio of hydrogen gas.

Subsequently, a recycled tire material was obtained by growing a microbial catalyst prepared by introducing a nucleic acid capable of coding isoprene synthase into a Clostridium microorganism, in the presence of the resulting gas containing the C1 gas. The recycled tire material was isoprene, and there was obtained a recycled tire in which about 70% of carbon components of the carbon monooxide component contained in the C1 gas had been converted into isoprene.

Subsequently, the resulting recycled tire material was polymerized, forming a polyisoprene rubber. A retreated tire was obtained by using the resulting polyisoprene rubber as a rubber component for constituting a tire and processing the isoprene rubber as a main material. The resulting retreaded tire was nearly new and was capable of being used for vehicles, such as a car.

Example 2

In Example 1, the microbial catalyst was exchanged to a metal catalyst, and thereby about 80% of the carbon components contained in the C1 gas was converted into ethanol. Moreover, ethanol was subjected to a dimerization reaction at high temperature, so that a recycled tire material was obtained. The recycled tire material was butadiene, and there was obtained a recycled tire in which about 80% of carbon components of the carbon monooxide component contained in the C1 gas had been converted into butadiene.

Subsequently, the resulting recycled tire material was polymerized together with styrene, forming a styrene-butadiene rubber. A retreated tire was obtained by using the resulting styrene-butadiene rubber as a rubber component for constituting a tire and processing the styrene-butadiene rubber as a main material. The resulting retreaded tire was nearly new and was capable of being used for vehicles, such as a car.

Example 3

In Example 1, the microbial catalyst was exchanged to a microbial catalyst prepared by introducing a nucleic acid capable of coding 1,4-butanediol synthase into a microorganism, and thereby about 70% of the carbon components contained in the C1 gas was converted into 1,4-butanediol. Moreover, 1,4-butanediol was subjected to a dehydration reaction at high temperature, so that a recycled tire material was obtained. The recycled tire material was butadiene, and there was obtained a recycled tire in which about 80% of carbon components of the carbon monooxide component contained in the C1 gas had been converted into butadiene.

Subsequently, the resulting recycled tire material was polymerized together with styrene, forming a styrene-butadiene rubber. A retreated tire was obtained by using the resulting styrene-butadiene rubber as a rubber component for constituting a tire and processing the styrene-butadiene rubber as a main material. The resulting retreaded tire was nearly new and was capable of being used for vehicles, such as a car.

Examples 1 to 3 show that a recycled material (e.g., a recycled tire material) capable of being used for obtaining a tire or the like can be obtained by obtaining a gas containing a C1 gas from a tire such as a waste tire, and then using the resulting gas containing the C1 gas. Examples 1 to 3 also show that a retreated tire can be obtained by obtaining a tire material (e.g., a recycled tire material) using a gas containing a C1 gas, and then using the resulting recycled tire material. Examples 1 to 3 show that a retreated tire can be obtained from a tire, such as a waste tire.

The invention claimed is:

1. A method for producing a tire, the method comprising:
a step of subjecting a tire to a gasification treatment to generate a gas comprising a C1 Gas from the tire,
a step of obtaining ethanol as an intermediate substance by using the gas comprising the C1 gas,
a step of obtaining a recycled tire material comprising at least one species selected from the group consisting of isoprene, butadiene, and polymers of these compounds by using the ethanol, and
a step of obtaining a tire by using the recycled tire material.

2. The method for producing a tire according to claim 1, wherein the tire to be used for the gasification treatment is a waste tire.

3. The method for producing a tire according to claim 1, wherein the gas comprising the C1 gas comprises $CO_x$ gas and hydrogen gas and x in the $CO_x$ gas is $1 \leq x \leq 2$.

4. The method for producing a tire according to claim 2, wherein the gas comprising the C1 gas comprises $CO_x$ gas and hydrogen gas and x in the $CO_x$ gas is $1 \leq x \leq 2$.

* * * * *